United States Patent [19]

Stanton

[11] 3,970,394
[45] July 20, 1976

[54] DENSITOMETER HEAD WITH FIBER OPTICS

[75] Inventor: Arthur J. Stanton, Warrensville Heights, Ohio

[73] Assignee: Harris Corporation, Cleveland, Ohio

[22] Filed: July 22, 1974

[21] Appl. No.: 490,397

[52] U.S. Cl. .................................. 356/195; 250/227; 356/212
[51] Int. Cl.² ...................... G01J 3/46; G01N 21/48
[58] Field of Search ............ 356/209, 210, 211, 212, 356/195; 250/227, 571, 572

[56] References Cited
UNITED STATES PATENTS

| | | | |
|---|---|---|---|
| 2,420,716 | 5/1947 | Morton et al. | 250/227 |
| 2,430,526 | 11/1947 | Mirfield et al. | 250/227 |
| 2,843,664 | 7/1958 | Olin | 250/227 |
| 3,136,310 | 6/1964 | Meltzer | 250/227 |
| 3,205,738 | 9/1965 | Ballmer et al. | 350/96 B |
| 3,393,602 | 7/1968 | Stouffer | 356/209 |
| 3,628,036 | 12/1971 | Humphrey | 250/227 |
| 3,698,813 | 10/1972 | Aisenberg | 250/227 |
| 3,756,725 | 9/1973 | Manring | 356/195 |

Primary Examiner—Vincent P. McGraw

[57] ABSTRACT

Densitometer head having a light source and optics for directing light onto a surface, optics and transducers for receiving and sensing light reflected from the surface, and external connections to signal processing circuitry. Fiber optics are used to receive the reflected light and transmit it to the sensors. The sensors, light source and optics are located in an in-line arrangement. Adjusting means are provided for adjusting the fiber optics relative to the light receiving optics and the sensors. The head is also provided with selected color filters which can be remotely selected. Purge air keeps the densitometer lenses clean.

9 Claims, 6 Drawing Figures

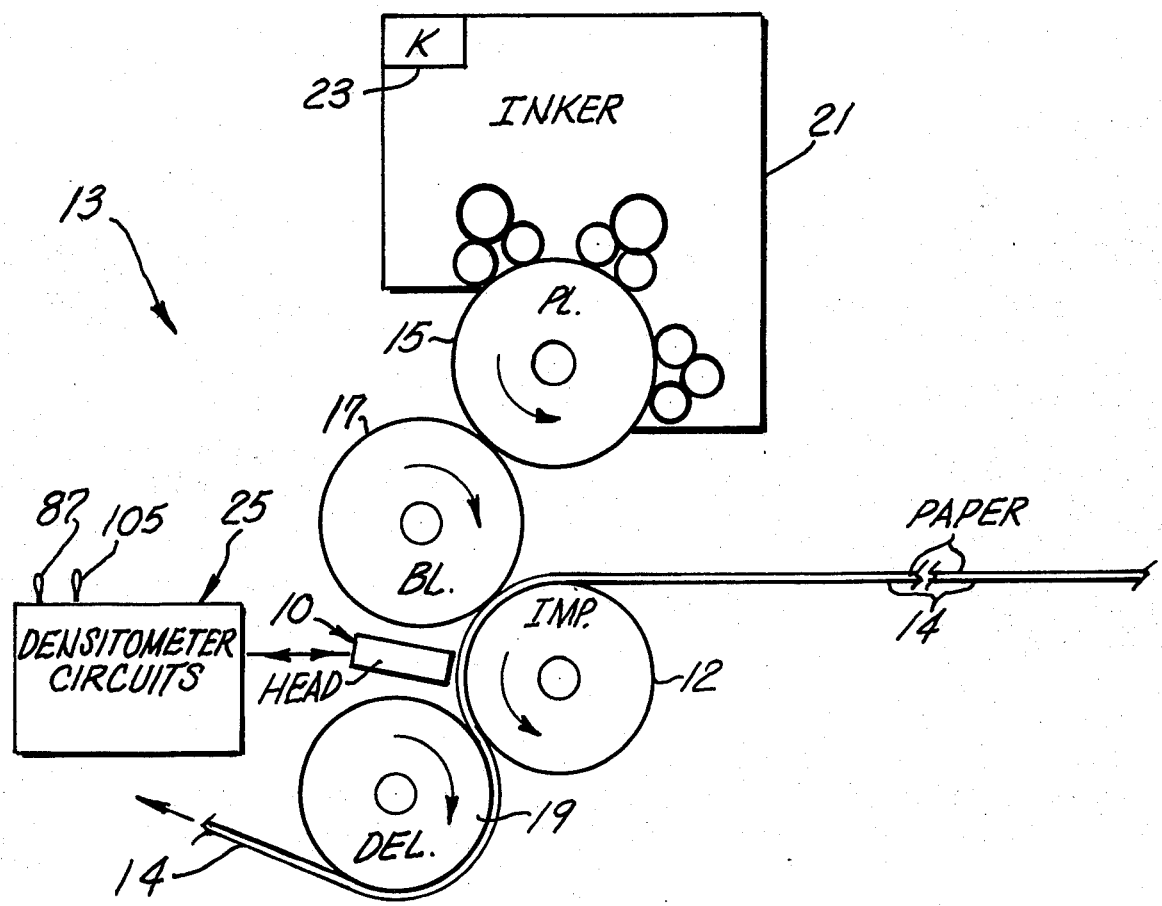
FIG.1
FIG.3
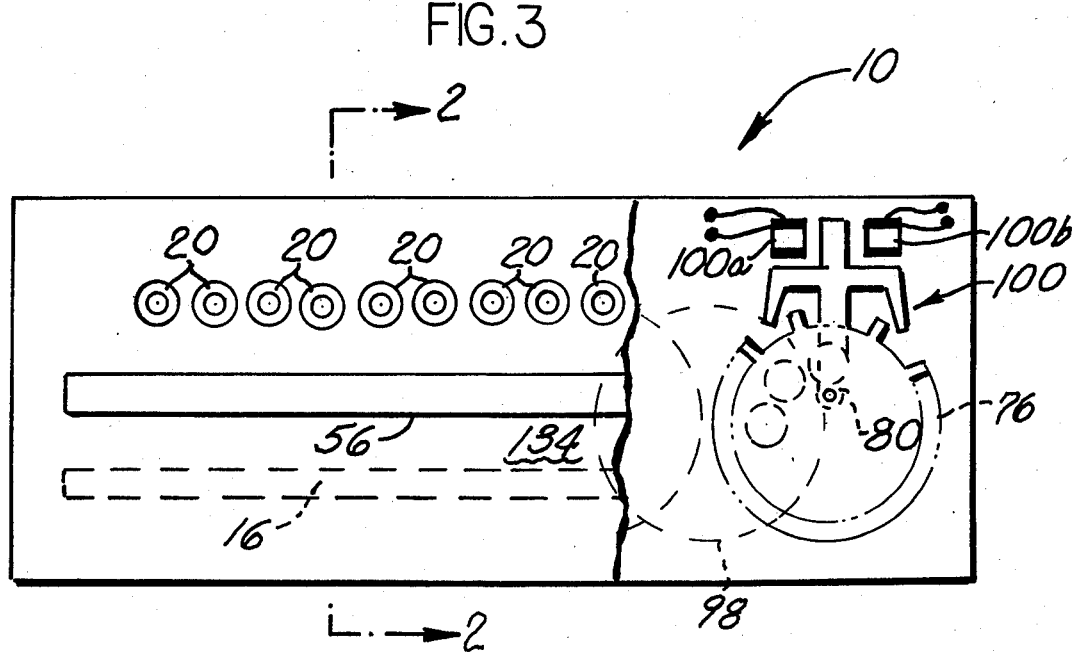

DENSITOMETER HEAD WITH FIBER OPTICS

BACKGROUND OF THE INVENTION

Printing presses of the prior art have been equipped with densitometers that illuminate the printed paper at the output of the press and measure the light reflected from the paper in order to measure the optical reflection density of ink being printed by the press. An operator can use the ink density reading as a guide for adjusting the rate at which ink is supplied to the printing press, to achieve a desired density of printed ink. One such densitometer is described in U.S. Pat. No. 3,756,725, issued Sept. 4, 1973, by J. Manring, and entitled Measurement and Control of Ink Density, which is incorporated herein by reference.

In other prior art it has been suggested that a flexible light pipe could be used to conduct light from a stationary lamp to a movable densitometer head to read density at various places, or to conduct reflected light received by a movable densitometer head to a stationary photosensitive detector.

Systems of the prior art are often so bulky that it is difficult to mount them on a printing press in a place where a reliable measurement of ink density can be obtained and where it is practical to replace color filters of the densitometer head to measure different colors of ink. Another problem that has been troublesome in densitometer heads of the prior art is that the lenses of the optical system become dirty very rapidly when the press is running, because of settling of airborne dry ink dust and of powder that is applied to the wet ink after printing to prevent undesired transfer of the ink. This necessitates frequent cleaning of the lenses in order to maintain the efficiency of the densitometer.

SUMMARY OF THE INVENTION

A densitometer head for measuring the optical density of a surface, e.g. ink printed by a printing press, includes a light source for simultaneously illuminating a printed test area whose ink density is to be measured and an unprinted reference area of the paper. Such a pair of areas is part of one density measurement channel. Light reflected from each of the areas enters a respective objective lens and is conducted through optical fibers to a photosensitive transducer. The optical fibers enable the transducer to be located farther away from the printed area being measured than the light source, and therefore to be generally in line with the light source. This enables the densitometer head to be narrow in transverse dimensions, which enables it to be mounted in small spaces.

In one aspect of the invention a plurality of channels, i.e. a plurality of pairs of test and reference densitometer light paths, are grouped in one densitometer head, with fiber optics for each path, in such a way that one critically narrow dimension of the densitometer head is the same for many channels as it is for one channel.

The fiber optics facilitate optical centering of the image to be measured on the photosensitive transducer by simple transverse adjustment of the ends of the flexible optical fibers.

In still another aspect of the invention an air pressure and shroud system is provided to keep the densitometer lenses clean so that mechanical cleaning is required only infrequently. This enables mounting the densitometer head in relatively inaccessible places.

Filter wheels may also be utilized in the head. Such wheels may contain a plurality of filters which are selectable by remote control, the remote control being possible because the fiber optics enable the filter wheels to be located away from the paper, where space is available for remotely controllable actuator apparatus.

Other aspects and features of the invention are apparent from the description and figures herein.

BRIEF DESCRIPTION OF FIGURES

FIG. 1 is a schematic showing of a lithographic printing press illustrating one possible location in the press for a compact densitometer head built in accordance with the present invention;

FIG. 3 is a front view of the densitometer head of FIG. 2, partially cut away;

DESCRIPTION OF A PREFERRED EMBODIMENT

Figure 2:
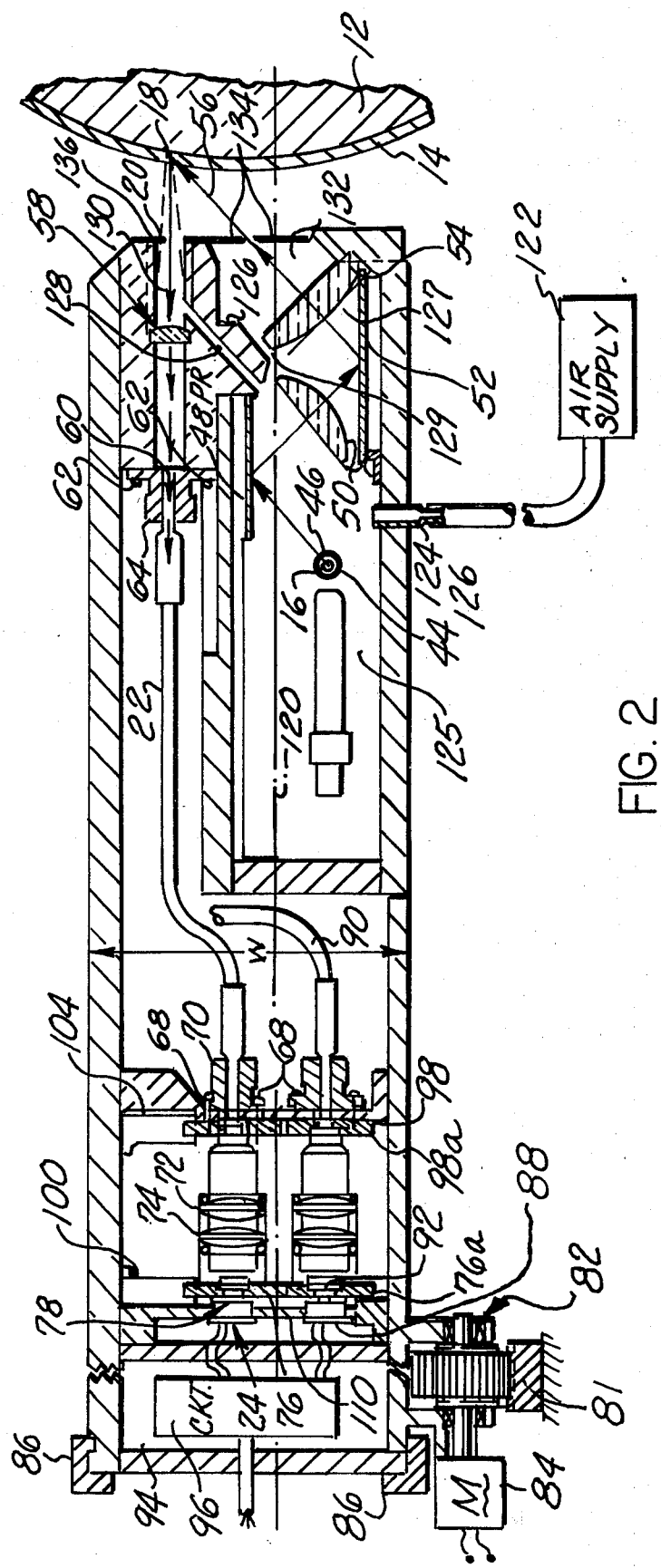
FIG. 2 is a cross-sectional side view of a densitometer head having six channels and illustrating the present invention.

The preferred embodiment of the invention illustrates the use of a densitometer head 10 embodying the present invention in a printing press. The head 10 is mounted near a cylinder 12 of the last printing unit 13 of a multiple unit lithographic printing press, FIG. 1.

Each printing unit of the press prints an image in a different color of ink on paper 14 as the paper travels successively through the printing units.

Only the last printing unit 30 of the printing press is shown in FIG. 3, and in schematic form. It has a plate cylinder 15, a blanket cylinder 17, the impression cylinder 12, and a delivery cylinder 19. Ink is provided to the plate cylinder 15 by an inker 21 comprising a multiplicity of inking rolls of various types. The rate of supply of ink is set by ink control keys 23, which are adjustable.

In the particular arrangement shown in FIG. 1 the densitometer head 10 is arranged to inspect the paper 14 as it passes over the impression cylinder 12, although the head 10 can be placed elsewhere, for example near the delivery cylinder 19, if preferred. Electrical output signals from the densitometer head 10 are connected by means of a cable to remotely located densitometer circuits 25, which are described in great detail in the above patent application 3,756,725. The densitometer circuits 25 supply signals and power as necessary to the densitometer head 10.

As shown in FIG. 2, light produced by a flash tube 16 illuminates an inspection region 18 of the paper 14, and light reflected from the inspection region 18 enters receiving ports 20. By means of optical fibers 22, the received light is conducted to a photosensitive transducer 24, which produces an electrical output signal in response to the light.

The densitometer head 10 being described, in connection with its remotely located electronic signal processing equipment 25, has capability for measuring as many as six different channels, for six colors, simultaneously. As shown in FIG. 3, the front of the densitometer head 10 has thirteen of the light receiving ports 20, corresponding to thirteen light paths, two of which are employed for each of the six color channels and one of which assists in adjusting the time at which the lamp flashes. Each color channel employs one of the ports 20 for receiving light reflected from a printed test patch and employs another of the ports 20 for receiving reference light reflected from an unprinted reference area adjacent to that printed test patch.

Figure 4:
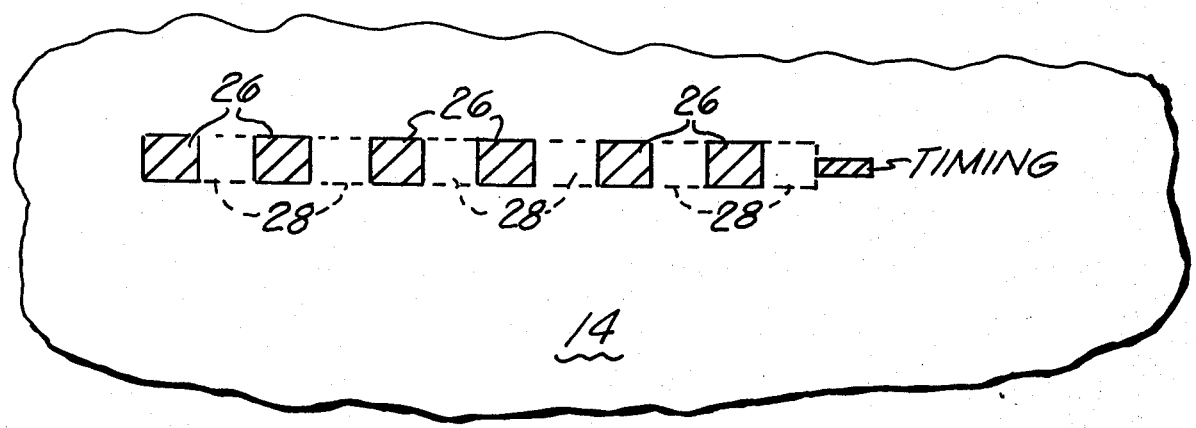
FIG. 4 depicts a row of test patches and reference areas printed on paper by the press.
Figure 6:
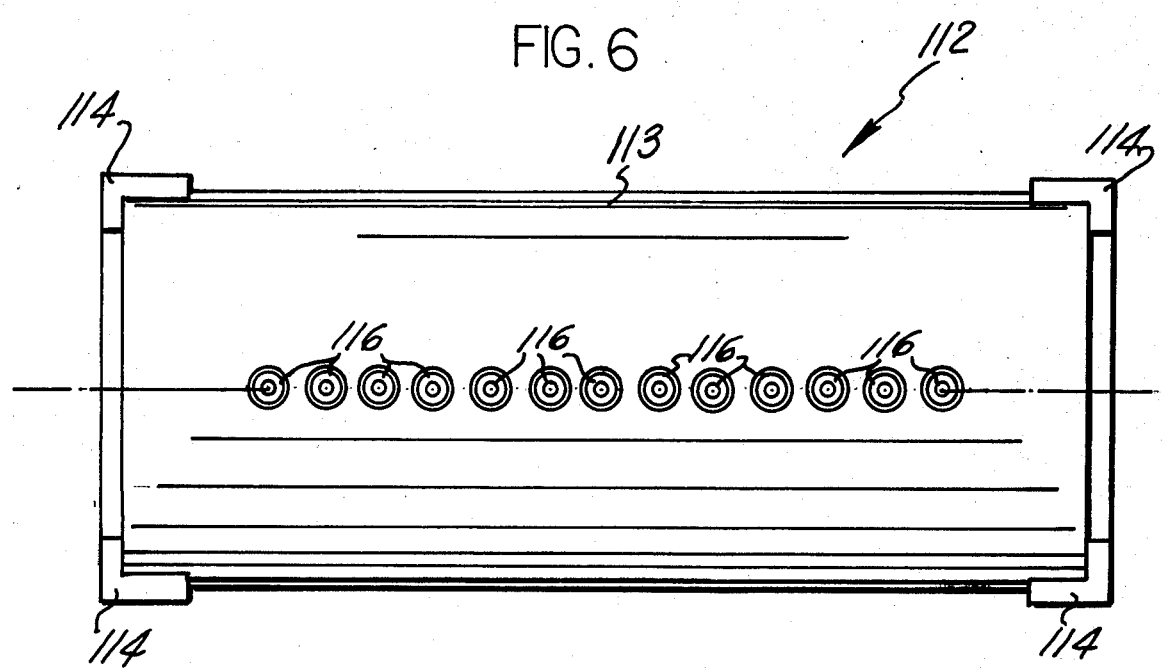
FIG. 6 shows a portion of an alignment fixture for use in transversely adjusting the input end of each optical fiber for placing it precisely at the area of the paper to be measured.
Figure 5:
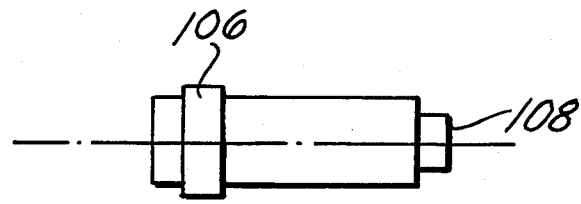
FIG. 5 shows an eyepiece and reticle for use in adjusting the transverse location of optical fibers in the densitometer head.

FIG. 4 shows printed test patches 26 on the paper 14 and an unprinted reference area 28 next to each of the test patch areas. The first patch 26 on the extreme left of FIG. 4 is viewed by the first port 20 at the extreme right of FIG. 2, and the unprinted reference area 28 adjacent the first test patch is viewed by the second port from the right, etc.

With reference again to FIG. 2, the light flash tube 16 is covered by a metal foil triggering electrode 44 except at its ends and except for a small angular area or window 46 through which light is omitted. A more uniform light flash is obtained when the triggering electrode 44 is wrapped almost completely around the tube in this manner. The flash tube 16 is electronically triggered to flash in synchronism with the arrival at the inspection region 18, of a row of printed test patches 26 and unprinted reference areas 28 on the paper 14. Synchronism is achieved by techniques described in the above patent.

Light from the flash tube 16 is reflected from a front surface mirror 48 and passes through a cylindrical lens 50 whose cylindrical axis is perpendicular to the plane of FIG. 2. The light patch is again folded, by reflection of the light from another front surface mirror 52, and the light then passes through a second cylindrical lens 54, whose cylindrical axis is parallel to that of lens 50. The light then passes out of the densitometer head 10 through a slit 56 and falls upon the inspection region 18 at approximately a 45° angle to the surface of the paper 14.

At the inspection region 18 some of the incident light is reflected in direction perpendicular to the surface of the paper 14, and into the circular ports 20. The reflected light that enters a port 20 passes through an achromatic lens 58, which produces an image of a portion of the region 18, at an input surface 60 of the fiber optics bundle 22. The transverse location of the fiber input surface 60 is adjustable by loosening two screws 62 and moving a holding bushing 64 up and down or into and out of the paper of FIG. 2.

The light is conducted through the fiber optics bundle 22 to an output surface 66 of that bundle. The transverse position of the output surface 66 is also adjustable by loosening two screws 68 and sliding a holding bushing 70 in any direction perpendicular to the direction in which light propagates in the fiber optics bundle 22.

Light emerging from the fiber output surface 66 travels through two sets of converging lenses 72, 74, which redirect the light through a turret type of filter wheel 76 and through an optical stop 78 onto a photosensitive transducer 24. The photosensitive transducer 24 produces and electrical output signal at its output leads in response to the light that it receives.

The filter wheel 78 has positions for holding eight filters such as filter 80, FIG. 3, and can be indexed manually to any of four positions. In each position of the wheel the topmost filter 80 and the lowest filter 92, which is diametrically opposite it, are in use, and the other six filters are idle. In a convenient arrangement one of the four filter positions has a pair of neutral density filters. A second position has a pair of red filters, the third position has a pair of green filters, and the fourth has a pair of blue filters.

The entire densitometer head 10 can be moved horizontally to different transverse positions along the width of the printing press by means of a drive mechanism comprising a stationary rack gear 81 and a pinion gear 82 driven by a remotely controlled bidirectional motor 84 on the head 10, FIG. 2. The densitometer head travels on a pair of guides 86. A three-position switch 87, FIG. 1, controls the motor 84.

At the same time that a reading is being made at a test patch 26 by the photosensitive transducer 24 another reading is being made by a photosensitive transducer 88 that receives light reflected from an unprinted reference area 28 along a path having an optical port 20, a lens similar to lens 58, an adjustment bushing similar to bushing 64, a fiber optics bundle 90, and the matched filter 92 in the lowest holder of the filter wheel 76.

As may be seen by reference to the right-hand cutaway portion of FIG. 3, the filter wheels 76 have such a large diameter that they would interfere mechanically with each other if alternate ones were not spaced forward in a different position as exemplified by the filter 98, FIG. 2. For densitometer channels for which a filter wheel is provided in the rearward position of wheel 76 there is no filter wheel in the forward position of wheel 98, and vice versa. This alternate staggering of filter wheels is done even though the fiber optics bundles such as bundles 22, 90 are able to be fanned out at the left end of FIG. 2 to twice the spacing they have at the right end, with the test and reference transducers of each channel being vertically disposed at the left end.

The filters 76, 98 can be rotated manually because an angular portion 76a, 98a respectively of each extends downward through the underside of the housing of the densitometer head 10. The filter wheels are conveniently set manually by counting clicks of a detent mechanism from the fully clockwise position toward the fourth position, which is fully counter-clockwise. The filters can also be moved to any of their four positions by means of bi-directional solenoid and ratchet devices 100, 104, which are operated by remote control. Each actuation of one of the solenoids, such as solenoids 100a, 100b, moves the corresponding filter wheel one detent position by means of a ratchet and pawl, unless the filter is already fully in the direction that it is being commanded to move. A switch 105, FIG. 1, is actuated in either of two directions to energize the solenoid and rotate the corresponding filter in a respective direction.

An electronic circuit compartment 94 is provided at the left side of the densitometer head 10, as shown in FIG. 2, to house preamplifiers and certain other circuit components 96.

The electrical signal produced in response to light reflected from a test patch area 26 is combined electronically with the electrical signal produced in response to light reflected from a respective unprinted reference area 28 adjacent to the printed area, the printed and unprinted areas being measured by matched pairs of equipment. A ratio of the test and reference signals is computed, and the logarithm to base 10 of that ratio is then computed to yield optical density.

The mechanical and optical centers of mounted lenses are frequently imperfectly aligned. According to the present invention, the fiber optics are aligned to place the received image of a selected portion of interest of the region 18 in the center of the optical system, and to deliver the image centrally onto the photosensitive transducer 24. The ends of each fiber optics bundle are adjusted transversely in a centering procedure to achieve the necessary image placement. To adjust a fiber optics bundle transversely to center the image, a light source is placed in front of the optical port 20 at the light input to the densitometer head 10, and the photosensitive transducer 24 is temporarily replaced by an eyepiece assembly 106, FIG. 4, which has a target reticle 108. When the eyepiece 106 is in place in the bulkhead 110, the longitudinal position on the light path of the target reticle 108 is located where the active area of the photosensitive transducer 24 would be located if that transducer were in place in the bulkhead 110.

An operator looks into the eyepiece 106, and with the screws 68 loosened he adjusts the positioning bushing 70 to center the received circular beam of light on the reticle 108. He then tightens the screws 68 to retain the bushing 70 in place.

The light source is next held at the left end of the light path in place of the photosensitive transducer 24. It transmits light through the fiber optics bundle 22 and produces a circular beam of light on the inspection region 18. A test gauge 112 is place at the inspection region 18 in a particular position with respect to the densitometer head 10, which is determined by positioning lugs 114 on the gauge 112 that engage corners of the densitometer head 10. The gauge 112 has a mylar reticle 113 that lies in contact with the surface of the inspection region 18 and which shows the desired location for the optical center of each light path. The screws 62 are loosened and the positioning bushing 64 is moved transversely to place the circular beam of light, which is being transmitted from left to right in FIG. 2, onto the center of a respective reticle pattern 116 of the mylar reticle 113. The screws 62 are then tightened and the photosensitive transducer 24 is again mounted in the bulkhead 110 for routine operation. This completes the centering procedure for the light receiving portion of the system.

Infrared filter glass may be interposed between the light source and the inspection region 18 to reduce the amount of infrared radiation employed, and coatings may be employed on the lenses 50, 54 for the same purpose.

The transducers 24, 88 and the large filter wheels 76, 98 are seen to be positioned remotely from the inspection region 18. These transducers and filter wheels are very generally on a common line 120 with the apparatus related to the light source 44, the line 120 being generally perpendicular to the surface of the inspection region 18. This enables the vertical dimension W of the densitometer head 10 to be relatively small because the transducer apparatus and the illumination apparatus are on the normal line 120 instead of being side by side parallel to an axis of the printing press cylinder 12. Also the width of each color channel is relatively narrow because, as shown in FIG. 2, the transducers 24, 88 for the test patch and reference area respectively can be arranged vertically as a result of the use of the optical fibers 22, 90, even though their respective input light ports 20 are horizontally aligned.

To prevent chaff, ink dust and ink drying powder from dirtying the lenses 54, 58, a source 122 of compressed air is connected to a hole 124 in a cavity 125 that houses the flash lamp 16. Air from the supply 122 passes from the cavity 125 over the lens 50 and into another illumination cavity 127, then over the lens 54 through an air channel 129 that is provided for this purpose, and into another cavity 132 at the output side of the lens 54.

The cavity 132 is enclosed by a sheet metal shroud 134 in which the light output slit 56 is formed, and air flows from the cavity 132 through the slit 56. This flow of air greatly reduces the amount of dirt that can get to the lens 54, so that the lens need not be cleaned very often.

Similarly, each lens 58 is kept clean by a flow of air from the air supply 122 through the cavity 125 and through a respective channel 128 into a light receiving path cavity 130, this air exiting by flowing through a respective one of the circular light ports 20, which are formed in a shroud 126.

Fiber optics can be used in the illumination optical path and/or the receiving optical path. The preferred embodiment of the invention described above illustrates the use of a fiber optic light path segment in a novel densitometer head to enable reduction of the transverse dimensions of the head so that the head can be placed in a small space where reliable optical density readings can be obtained. Moreover, the preferred embodiment illustrates the use of filter wheels that are settable to select filters either manually at the densitometer head or electronically by remote control, and illustrates further the use of shrouds and compressed air to keep the illumination and sensor path lenses clean in the dusty environment of a printing press.

What is claimed is:

1. A densitometer head comprising a housing having first and second opposing walls, said first wall having apertures therein from which light is directed to a surface and reflected light received therefrom, a light source disposed in said housing for directing light therefrom onto the surface to be tested, first optical elements disposed between said light source and said first wall for directing the light onto the surface to be tested, second optical elements proximate said first wall for receiving light reflected from the surface, transducers for sensing the light received from the surface and disposed adjacent said second wall, light transmitting means comprising at least one fiber optics element per transducer for conducting light from said second optical elements to said transducers, said fiber optics elements extending from a location intermediate said first wall and said light source and extending to said transducers, and electrical circuit means for connecting said transducers to processing circuitry external of the head, each of the fiber optics elements in said head for conducting light to said transducers has first and second adjusting means connected respectively to the opposite ends of the fiber optics element to adjust the optical alignment transversely of the light received by and transmitted from the ends of the fiber optics elements, said fiber optics elements being flexible.

2. The densitometer head as defined in claim 1 wherein said first wall has a slit aperture from which light is directed onto a plurality of test surfaces and a corresponding plurality of apertures for receiving light from the test surfaces, there being a transducer for each aperture for receiving light from a respective surface.

3. The densitometer head as defined in claim 2 and wherein said first optical elements comprise optical elements adjacent said first wall for directing light from said light source through a first aperture in said first wall, and wherein said second optical elements comprise a plurality of optical elements adjacent said first wall for receiving light reflected from said test surface through a corresponding plurality of respective receiving apertures.

4. A densitometer head as defined in claim 3 and further comprising a first cavity within said head for enclosing said light source, means communicating with said first cavity for conducting air under pressure thereto from an external source of air, a second cavity between said first optical elements and said first wall, means for conducting air from said first cavity around said first optical elements to said second cavity to enable the air to flow out of said first aperture, a plurality of third cavities each located intermediate one of said second optical elements and a respective one of said receiving apertures, and a plurality of means each for conducting air from said first cavity to a respective one of said third cavities to enable the air to flow out of said receiving apertures.

5. A densitometer head comprising a housing having first and second opposed walls, said first wall forming a viewing face for the densitometer head and having apertures laterally spaced therein for directing light onto a surface to be tested and for receiving light therefrom, means for directing light from said first wall onto the surface to be tested comprising a lamp disposed within said head, means for receiving light reflected from the surface through a light receiving aperture in said first wall comprising a lens element having an optical centerline, a light sensor disposed within said head, a flexible fiber optics element for conducting light received from said lens element to said sensor, first adjusting means connected to the end of said fiber optics element adjacent said lens element to align the fiber optics element transversely of the optical axis of said lens element, and second adjusting means connected to the end of said fiber optics element adjacent said sensor to effect alignment of that end of the fiber optics transversely of an optical axis for transmitting light to said sensor.

6. A densitometer head comprising
   a housing having an apertured face for transmitting light,
   a light source arranged in said housing for illuminating an external surface disposed proximate said face, said surface having both a test area whose optical reflection density is to be measured and a density reference area,
   sensing means in said housing including first and second photosensitive transducers receiving light reflected from said test area and from said reference area respectively for producing first and second respective electrical signals,
   said sensing means and said light source being disposed in fixed relationship to each other and to said face, and generally along a common line extending from said face, said sensing means and said source being at different distances from said face,
   light conducting means comprising fiber optics means for conducting light along at least part of a distance between sensing means,
   said fiber optics means comprises optical components including at least one flexible fiber optics light path element and means for adjustably positioning at least one end of said fiber optics light path element transversely to the direction of light propagation in the light path, for optically aligning said fiber optics light path element with other of said optical components.

7. A densitometer head as defined in claim 6 and further comprising an optical filter holder, holding a plurality of filters, in a light path intermediate said face and said transducer means, said filter holder being rotatable to selectively locate different filters of said plurality in said light path.

8. A densitometer head as defined in claim 7 and further comprising actuator means proximate said filter holder and energizable to rotate said holder to selectively locate said filters in said light path, and control means remote from said densitometer head for energizing said actuator means to select a filter.

9. A densitometer head as defined in claim 6 and further comprising a first lens transmitting light intermediate said light source and said surface, said face comprising a first shroud defining a light opening intermediate said first lens and said surface, a second lens transmitting light intermediate said surface and said optical sensing apparatus, said face further comprising a second shroud defining a light opening intermediate said second lens and said surface, and means for forcing air through said openings away from each of said lenses toward said face to reduce collection of dirt on said lenses.

* * * * *